US012702410B2

(12) United States Patent
Burnet et al.

(10) Patent No.: US 12,702,410 B2
(45) Date of Patent: Aug. 11, 2026

(54) APPARATUS AND METHOD FOR IDENTIFICATION AND MEASUREMENT OF INTRAMEDULLARY LENGTH

(71) Applicant: Zimmer, Inc., Warsaw, IN (US)

(72) Inventors: Paige Elizabeth Burnet, Warsaw, IN (US); William Scott Van Dyke, Warsaw, IN (US); Monty J. Lackey, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 478 days.

(21) Appl. No.: 18/136,735

(22) Filed: Apr. 19, 2023

(65) Prior Publication Data

US 2023/0338022 A1 Oct. 26, 2023

Related U.S. Application Data

(60) Provisional application No. 63/333,343, filed on Apr. 21, 2022.

(51) Int. Cl.
*A61B 17/072* (2006.01)

(52) U.S. Cl.
CPC .. *A61B 17/072* (2013.01); *A61B 2017/07214* (2013.01); *A61B 2017/07285* (2013.01)

(58) Field of Classification Search
CPC .......... A61C 5/44; A61C 1/082; A61B 17/17; A61B 17/16; A61B 17/1615; A61B 17/1617; A61B 17/162; A61B 17/1622; A61B 17/1631; A61B 17/1633; A61B 17/164; A61B 17/1655; A61B 17/1624; A61B 17/3207; A61B 17/320725; A61B 17/320758; A61B 2017/320766; A61B 2017/320775; A61B 17/320783; A61B 2017/320791; A61B 2090/033; A61B 2090/036; A61B 17/80;
(Continued)

(56) References Cited

U.S. PATENT DOCUMENTS 6,004,320 A * 12/1999 Casscells ......... A61B 17/32002 606/49
6,214,001 B1 * 4/2001 Casscells ............. A61B 18/148 606/49
(Continued)

FOREIGN PATENT DOCUMENTS

WO WO 2021/087126 * 5/2021

*Primary Examiner* — Thomas McEvoy
(74) *Attorney, Agent, or Firm* — Schwegman Lundberg & Woessner, P.A.

(57) ABSTRACT

A removable intramedullary canal measurement instrument is discussed herein. The measurement instrument can include an elongate body connecting an adapter clip with a plurality of measurement clips. The elongate body can extend from a first end to a second end along a longitudinal axis. The adapter clip can extend perpendicular to the longitudinal axis from the first end and be configured to secure the measurement device to a portion of a reaming instrument. Finally, the plurality of measurement clips can be distributed along the elongate body at known distances from a cutting tip of the reaming instrument when the measurement device is secured to the portion of the reaming instrument, each measurement clip of the plurality of measurement clips can be configured to engage a shaft of the reaming instrument.

13 Claims, 13 Drawing Sheets

(58) Field of Classification Search
CPC .......... A61B 2017/00486; A61B 90/11; B23B 49/003; B23B 49/005; B25F 5/003; Y10T 408/953; A61F 2002/4662; A61F 2002/4658; A61M 2025/024
See application file for complete search history.

(56) References Cited

U.S. PATENT DOCUMENTS

| | | | | |
|---|---|---|---|---|
| 2005/0107819 | A1* | 5/2005 | Sater | A61M 25/00 604/528 |
| 2018/0140378 | A1* | 5/2018 | Ebrahimi | A61B 1/24 |
| 2019/0264040 | A1* | 8/2019 | Gilbert | C09D 7/69 |
| 2021/0298768 | A1* | 9/2021 | Biton | A61B 17/16 |

* cited by examiner 400
420D
420C
420B
420A
425
410
460
150
415

420D
420C
420B
420A
320
340
360
380
425
410
415

500
410
550
510

500
525
520
515
510
550

5D
5D
515
510
550

APPARATUS AND METHOD FOR IDENTIFICATION AND MEASUREMENT OF INTRAMEDULLARY LENGTH

CLAIM OF PRIORITY

This application claims the benefit of U.S. Provisional Patent Application Ser. No. 63/333,343, filed on Apr. 21, 2022, the benefit of priority of which is claimed hereby, and which is incorporated by reference herein in its entirety.

TECHNICAL FIELD

This document pertains generally, but not by way of limitation, to measurement instruments to assist in determining the depth of reaming with an intramedullary reaming instrument. More specifically, but not by way of limitation, the present application relates to a removable measurement apparatus for use with an intramedullary reaming instrument.

BACKGROUND

Intramedullary nails are used to assist in repair of leg fractures, among other things. In order to insert an intramedullary nail, the intramedullary canal must be reamed to a sufficient depth to receive the appropriate length nail. Traditionally, measurement of intramedullary nail lengths is performed either external to the bone with estimation techniques or through use of a separate intramedullary measurement instrument under fluoroscopy. Both techniques require additional operations, with the separate intramedullary measurement instrument in combination with fluoroscopy requiring additional steps within the surgical procedure. Accordingly, there is a need for a measurement device that does not require a separate step in the surgical procedure.

OVERVIEW

The present inventors have recognized, among other things, that a problem to be solved can include enabling fluoroscopy-based intramedullary canal length measurement during the intramedullary reaming procedure. The present invention allows surgeons to determine intramedullary length during the reaming process. The apparatus discussed herein allows surgeons to measure common nail lengths using fluoroscopy without an additional step of using a separate nail length gauge, which saves surgical steps and time. Unlike current alternatives, the removable (clip-on) measurement apparatus discussed herein allows intramedullary length to be measured during the reaming process using fluoroscopy. Commonly used alternatives to the disclosed device include x-ray templates and rulers off of guidewires. The disclosed device provides more accurate results than x-ray templates as it does not rely on a magnification factor. The disclosed device is easier to use than rulers because it does not rely on proper guidewire or ruler placement to accurately measure intramedullary length. Finally, the disclosed device saves surgical time by eliminating a separate step of inserting a nail depth gauge subsequent to the reaming process.

The present subject matter can provide a solution to the problem identified above by providing a removable measurement device that is removably attachable to a reamer shaft and adapter end. In other words, the measurement device (instrument) discussed herein can clip or snap onto a reamer instrument. For example, in some embodiments the measurement instrument clips onto a Hudson adapter (or any power drill adapter) and maintains a constant distance from the reamer tip, allowing for accurate intramedullary length measurements throughout the full reaming process. In certain embodiments, the measurement instrument includes four measurement clips at common nail lengths, such as 320 mm, 340 mm, 360 mm, and 380 mm. In an example, the nail length is measured off the trailing edge of the measurement clips. In other examples, the nail length may be measured off different portions of the measurement clips. The instrument is flexible such that it bends with the curvature of a flexible reamer shaft. The measurement clips are radiopaque, with the remainder of the instrument being any suitable materials such as metal or plastic.

This overview is intended to provide an overview of subject matter of the present patent application. It is not intended to provide an exclusive or exhaustive explanation of the invention. The detailed description is included to provide further information about the present patent application.

Figure 1A:
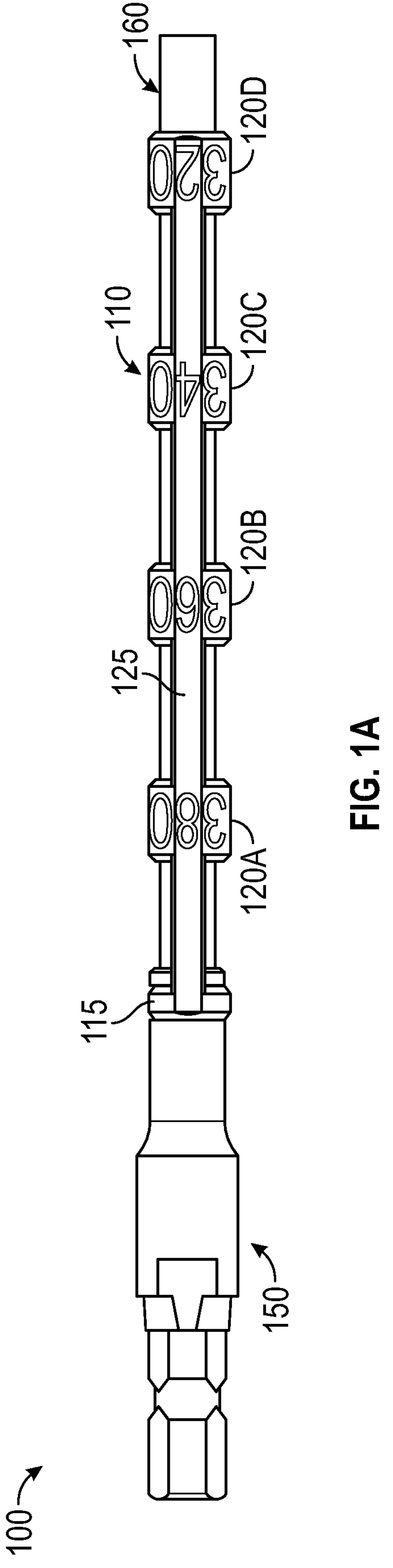
FIGS. 1A-1C are various views illustrating a removable intramedullary measurement instrument attached to a reaming instrument, according to an example embodiment.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document. As alluded to in the drawing descriptions and further detailed below, many of the illustrated example structures can be utilized across different embodiments, as would be understood by a person of ordinary skill in the art.

DETAILED DESCRIPTION

The removable (clip-on) intramedullary canal measurement instrument discussed herein is designed for use with a flexible intramedullary canal reamer that prepares an intramedullary canal to receive an intramedullary nail (e.g., femoral nail, tibial nail, etc.). Intramedullary nails are used to assist in various fracture repairs and reconstructions of the femur or tibia, among other bones. Intramedullary nails are indicated for femoral fractures, such as intertrochanteric, basi/trans-cervical femoral neck fractures, subtrochanteric fractures, ipsilateral femoral neck/shaft fractures, segmental fractures, nonunions and malunions, polytrauma, and various reconstructions. Tibial nails are similarly designed to treat various fractures of the tibia. Nailing techniques involve reaming out an intramedullary canal, inserting a nail into the intramedullary canal, and then securing the implant (nail) with screws to maintain length and alignment while healing occurs. While the measurement instrument disclosed herein is discussed in reference to intramedullary nailing, a person of ordinary skill would recognize potential uses outside of intramedullary nailing.

Figure 1B:
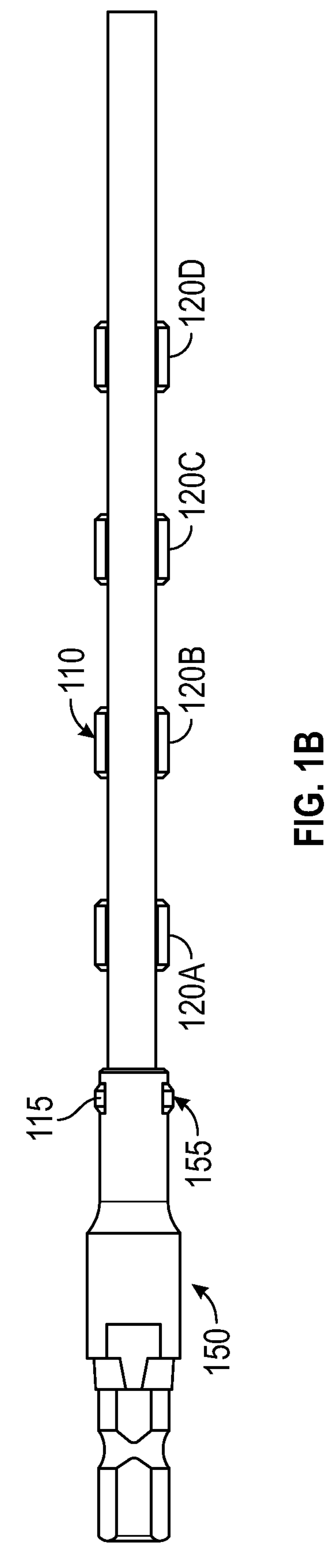
Figure 1C:
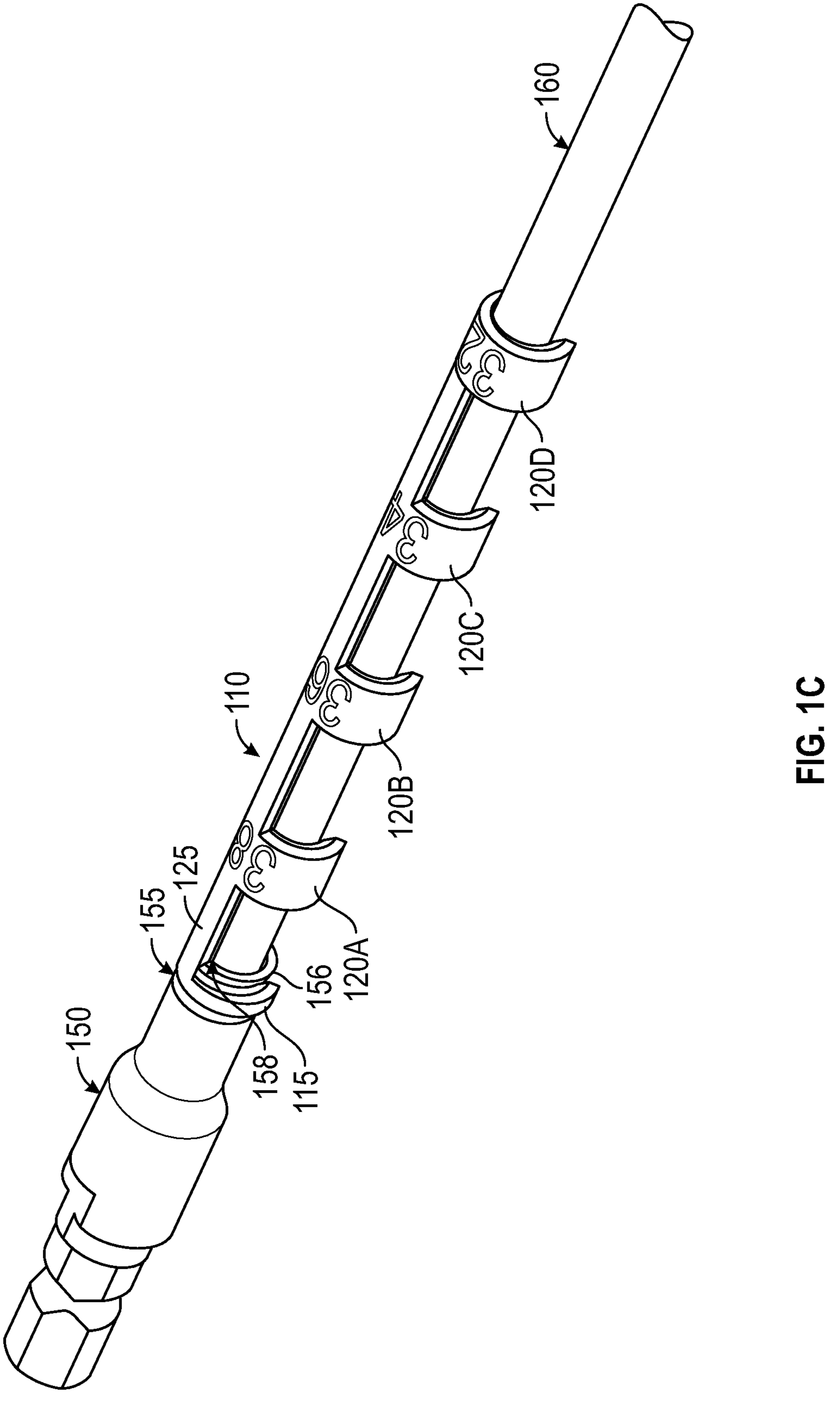

FIGS. 1A-1C are various views illustrating a removable intramedullary measurement instrument 100 attached to a reaming instrument, according to an example embodiment. The example instrument 100 is discussed in reference to all of FIGS. 1A to 1C concurrently. In this example, the clip-on intramedullary measurement instrument 100 is illustrated temporarily attached to a modified Hudson adapter 150 and a flexible shaft 160 of a reaming instrument. The modified Hudson adapter 150 includes a slot or channel, such as clip channel 155, to receive an adapter clip 115 of the measurement instrument 100. As noted previously, the illustrated modified Hudson adapter 150 is representative of any power drill adapter that may be used in conjunction with a reaming instrument. The clip channel 155 ensures that the measurement instrument 100 is coupled in a consistent orientation relative to the reaming tip of the reaming instrument allowing the measurement instrument 100 to provide measurements relative to the reaming tip. The adapter clip 115 includes an inner diameter such that it creates a friction fit with the shaft 160 exposed by the clip channel 155. The drive adapter 150 also includes a drive retention clip 156 distal of the clip channel 155 to hold the measurement instrument 100 in a known orientation (e.g., distance) from the reamer tip (not illustrated). In this example, the modified drive adapter 150 also includes an elongate body groove 158 that extends through the drive retention clip 156 to allow the elongate body 125 to extend distally from the adapter clip 115. An example drive adapter 150 is illustrated in FIGS. 3A-3B discussed below.

In this example, the measurement instrument 100 includes four (4) measurement clips 120A-120D (collectively referenced as measurement clips 120). The measurement clips 120 are each positioned along an elongate body 125 at distances that correspond with common intramedullary nail lengths, in this example at 380 mm, 360 mm, 340 mm, and 320 mm. The measurement lengths are from the tip of the reaming instrument (or from a distance representative of how far an intramedullary nail would extend into the reamed canal). The measurement clips 120 are configured to removably attach to the flexible shaft 160 of the reaming instrument. In certain examples, the measurement clips 120 are all configured to create a friction fit with the flexible shaft 160. In other examples, only the distal measurement clip, such as measurement clip 120D, is configured to create a friction fit with the shaft 160. In these examples, the other measurement clips 120A-120C are configured to slip over the shaft without any or with minimal friction.

The measurement instrument 100 is intended for use under intraoperative fluoroscopy (x-ray or similar medical imaging) to allow a surgeon to determine intramedullary canal length to enable selection of appropriate nail length for the application. In an example, the measurement clips 120 are formed from a radiopaque material to enable easy identification of measurement lengths within a fluoroscopic image. In the illustrated example, the measurement clips 120 are all illustrated as being identical other than the etched measurement numbers. In this example, different lengths are identified solely by position along the elongate body 125. In some examples, the elongate body 125 is not radiopaque to avoid interference with the measurement clips when imaging. In certain examples, a radiopaque material may be embedded into the measurement clips 120, while the remaining structure of the measurement instrument 100 is a suitable biocompatible material. In certain examples, each measurement clip 120 is visually unique (beyond the etched numbers), such as each measurement clip 120 can be a different width (length) along the elongate body 125. Each measurement clip 120 being a different width may enable easier identification of the different clips within a fluoroscopic image. Other unique shapes or even radiopaque numbers could be embedded within the measurement clips 120 to facilitate identification within a fluoroscopic image. As rotational orientation relative to the fluoroscope cannot be guaranteed, unique shapes that are rotationally consistent will ensure a consistent display within the fluoroscopic image (such as different widths or different numbers of strips (e.g., cylindrical strips of radiopaque material within the measurement clip)).

Figures 2A, 2B:
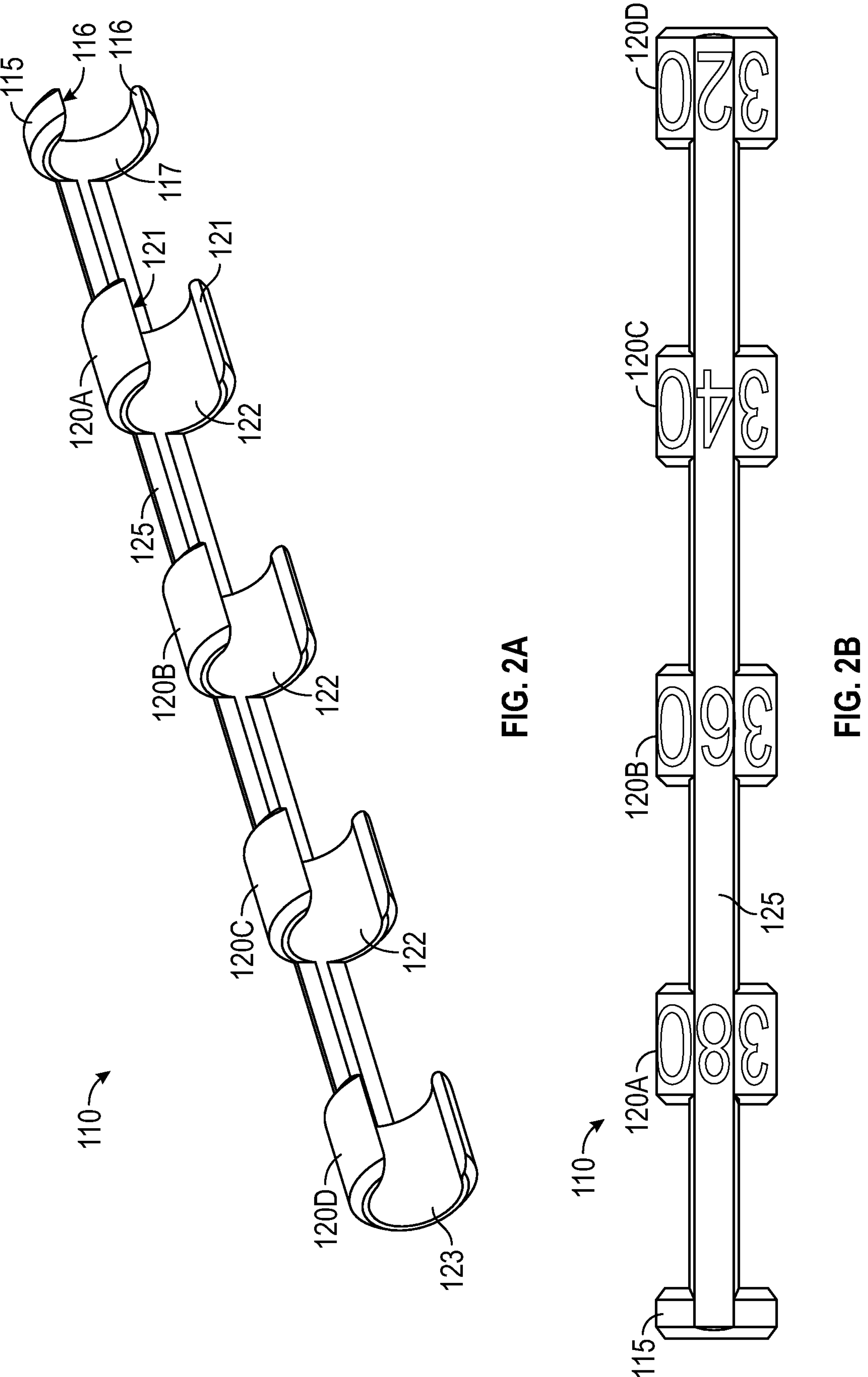
FIGS. 2A-2C are various views illustrating a removable (clip-on) intramedullary measurement device, according to an example embodiment.
Figures 2C, 3A:
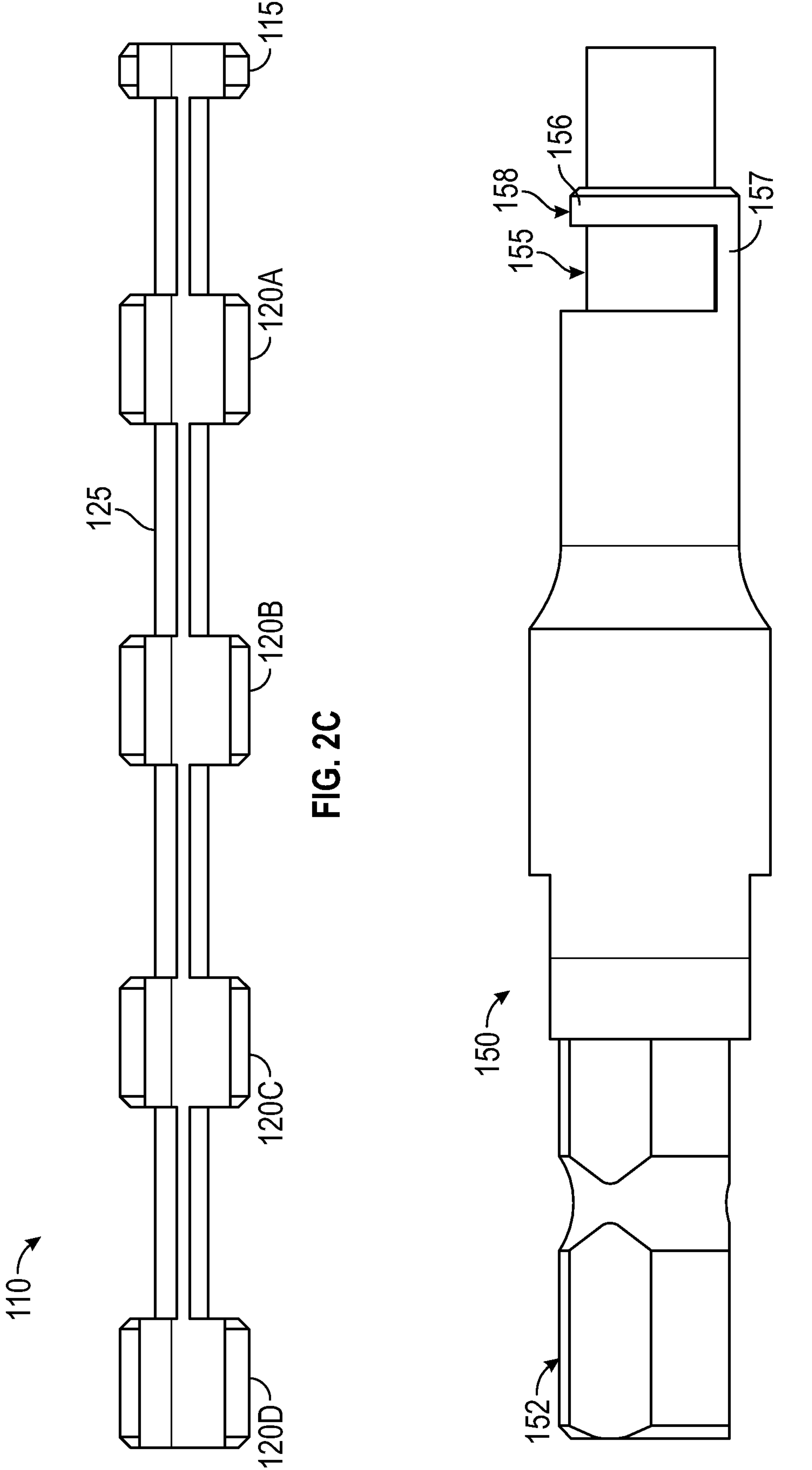
FIGS. 3A-3B are various views illustrating a modified Hudson adapted for use with a removable measurement instrument, according to an example embodiment.
Figure 3B:
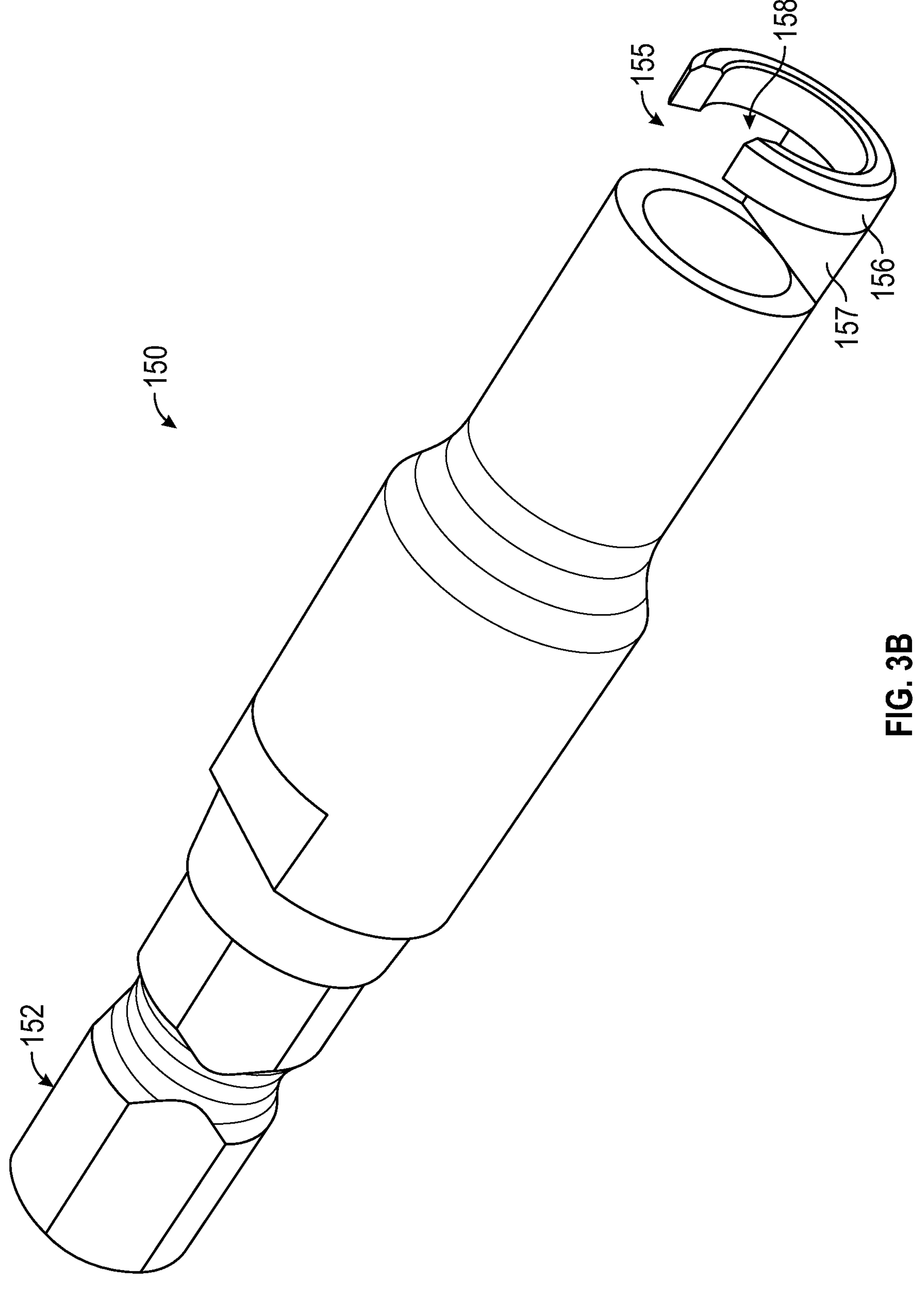

FIGS. 2A-2C are various views illustrating a removable (clip-on) intramedullary measurement device 110, according to an example embodiment. These figures provide views of the measurement device 110 separated from the reaming instrument. In this example, the measurement device 110 includes an adapter clip 115 and measurement clips 120 connected together by an elongate body 125. Each of the measurement clips 120 can include inner clip diameters 122, 123. As discussed above, the inner clip diameter 123 can be slightly smaller than inner clip diameter 122 to generate a friction fit for measurement clip 120D. In other embodiments, all inner clip diameters 122, 123 are sized to create a friction fit. The measurement clips 120 can also include chamfered edges 121 to ease installation on the reamer shaft 160.

The measurement device 110 is secured to a drive adapter via adapter clip 115 on the proximal end of the elongate body 125. In this example, the adapter clip 115 includes an inner adapter clip diameter 117 and chamfered edges 116. The adapter clip diameter 117 is configured to create a secure fit with the shaft 160 within the clip channel 155. In an example, the adapter clip diameter 117 is sized to create a friction fit on the shaft 160, which can be a flexible reamer shaft.

FIG. 3A is a side view of a modified Hudson adapter 150 for use with a removable measurement instrument, according to an example embodiment. In this example, the drive adapter 150 is a modified Hudson adapter. In other examples, the drive adapter can be a modified AO (large or small) adapter and any other suitable drive adapter used for intramedullary reaming instruments. The modifications to the adapter involve accommodating the clip-on measurement device 100. In an example, the drive adapter 150 includes a drive interface 152, a clip channel 155, a drive retention clip 156, an attachment extension 157, and an elongate body groove 158. The modifications are on the distal end of the drive adapter 150 and include the clip channel 155, which is a removed section of material configured to receive the adapter clip 115 of the measurement device 100. Distal of the clip channel 155 is a drive retention clip 156, which is a cylindrical C-shaped ring of material connected to the main body of the drive adapter 150 by the attachment extension 157. The drive retention clip 156 includes a groove (or separation) to from the elongate body groove 158, which allows the elongate body 125 of the measurement device 100 to extend distally from the adapter clip 115. The adapter clip 115 and the drive retention clip 156 are essentially mirror images of each other and cooperate to secure the longitudinal position of the measurement device 100 along the length of the reaming instrument.

FIG. 3B is an isometric view of the modified Hudson adapter 150 that provides an additional view of structures such as the drive retention slip 156 and the attachment extension 157. FIG. 3B also provides a different perspective to further illustrate the clip channel 155 and the elongate body groove 158.

Figures 4A, 4B:
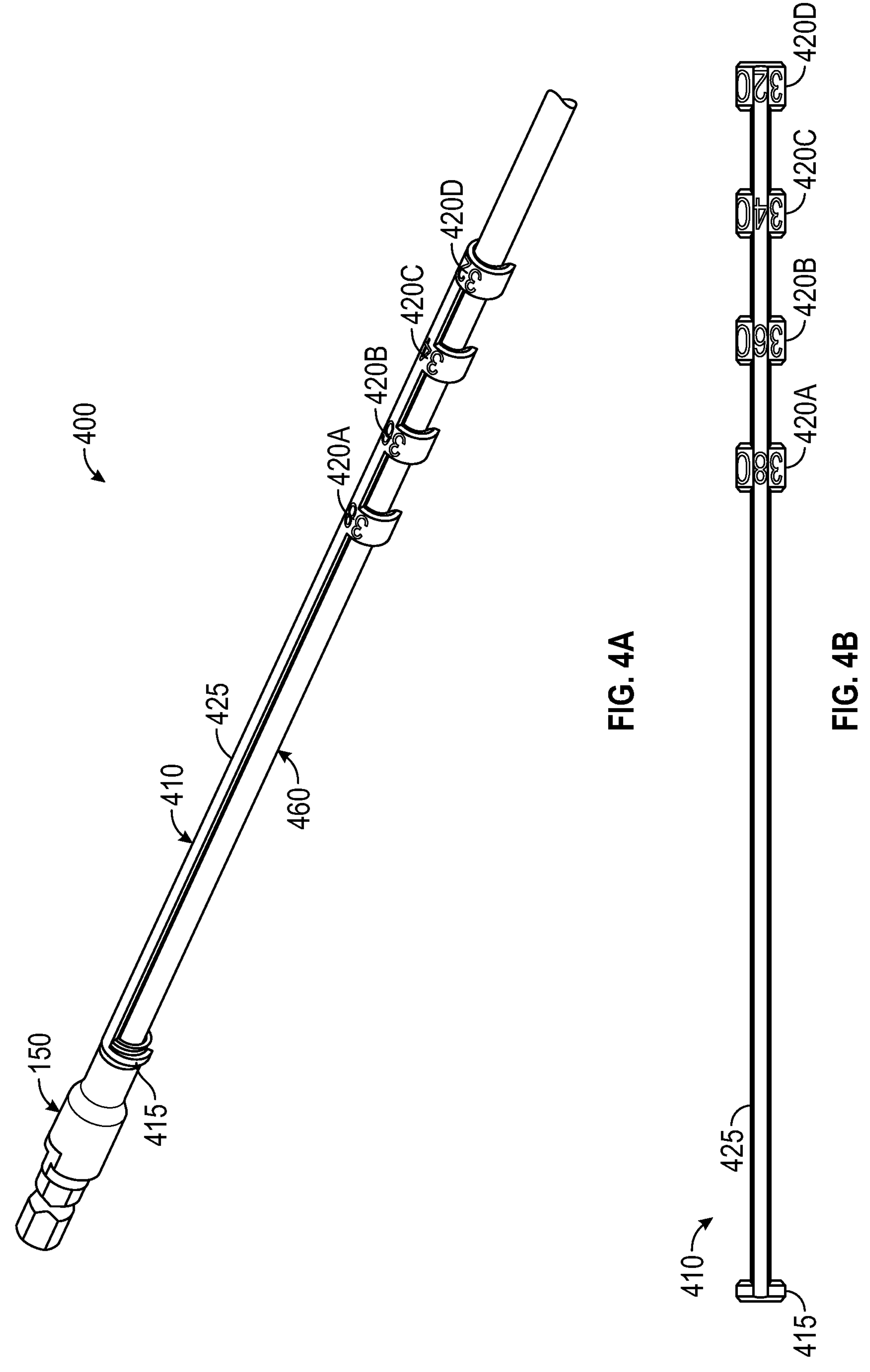
FIGS. 4A-4B are various views of a long removable intramedullary canal measurement instrument, according to an example embodiment.

FIGS. 4A-4B are various views of a long removable intramedullary canal measurement instrument 410, according to an example embodiment. In this example, the measurement instrument (device) 410 is similar to measurement device 110 but includes an extended section of the elongate body 425. The reaming instrument 400 illustrated in these figures includes a long clip-on measurement instrument 410 that comprises an adapter clip 415 and four measurement clips 420A-420D connected together by elongate body 425. The elongate body 425 of the clip-on measurement instrument 410 includes an extended section between the adapter clip 415 and the first measurement clip 420A. Other structures and features of the long clip-on measurement instrument 410 are the same as those of the clip-on measurement instrument 110, such as measurement clip positioning and structure.

FIGS. 5A-5E are various views of a spring-loaded adapter 510 for retaining a removable intramedullary canal measurement instrument 110, 410, according to an example embodiment. In this example, the modify drive adapter 550 includes a spring-loaded (biased) retention mechanism 510 that captures the adapter clip 415 of the long clip-on measurement instrument 410. The spring-loaded retention mechanism 510 is similarly compatible with the clip-on measurement instrument 110 (e.g., can retain adapter clip 115 in a manner similar the adapter clip 415).

Figure 5A:
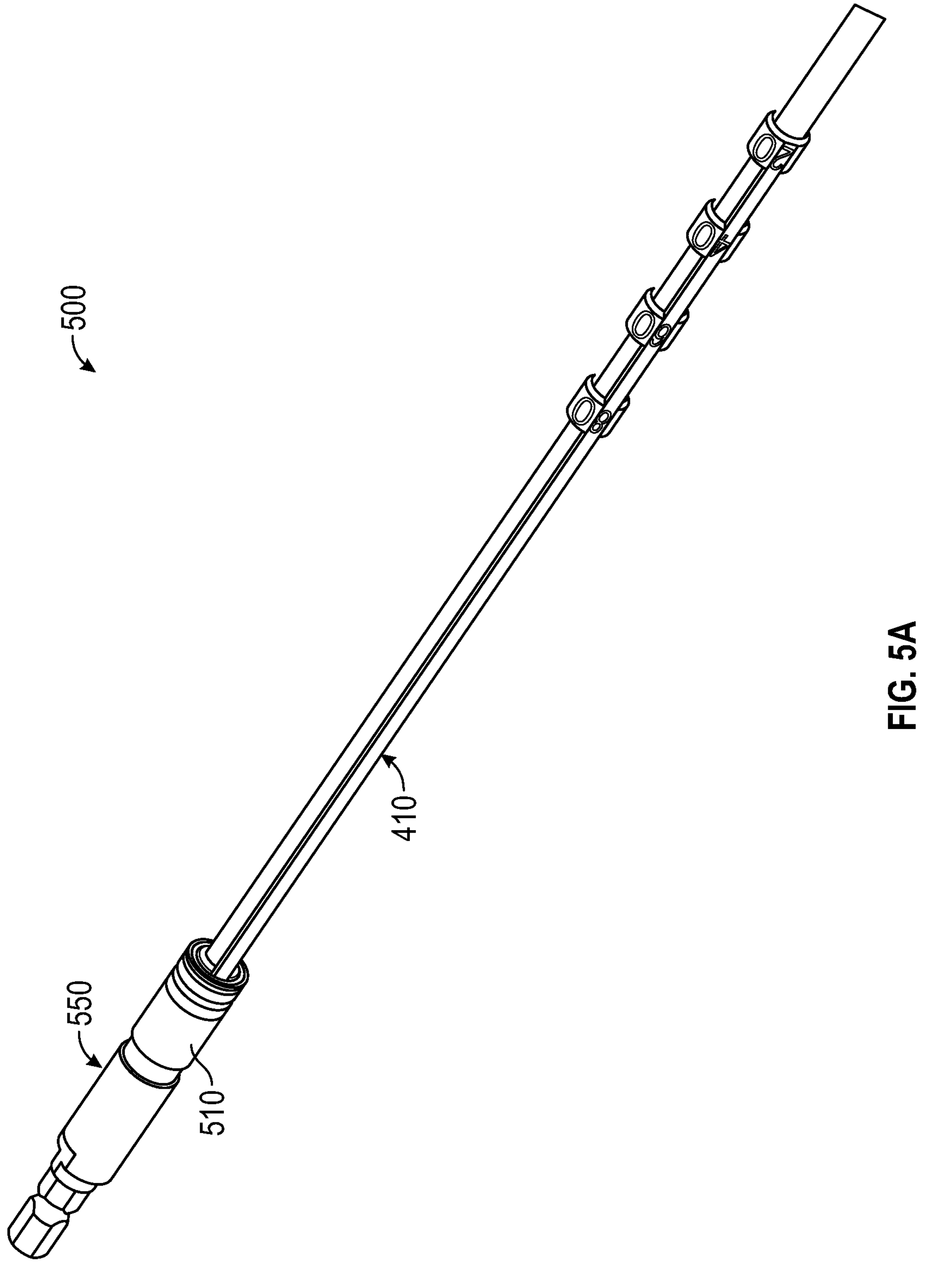
FIGS. 5A-5D are various views of a spring-loaded adapter for retaining a removable intramedullary canal measurement instrument, according to an example embodiment.
Figures 5B, 5C:
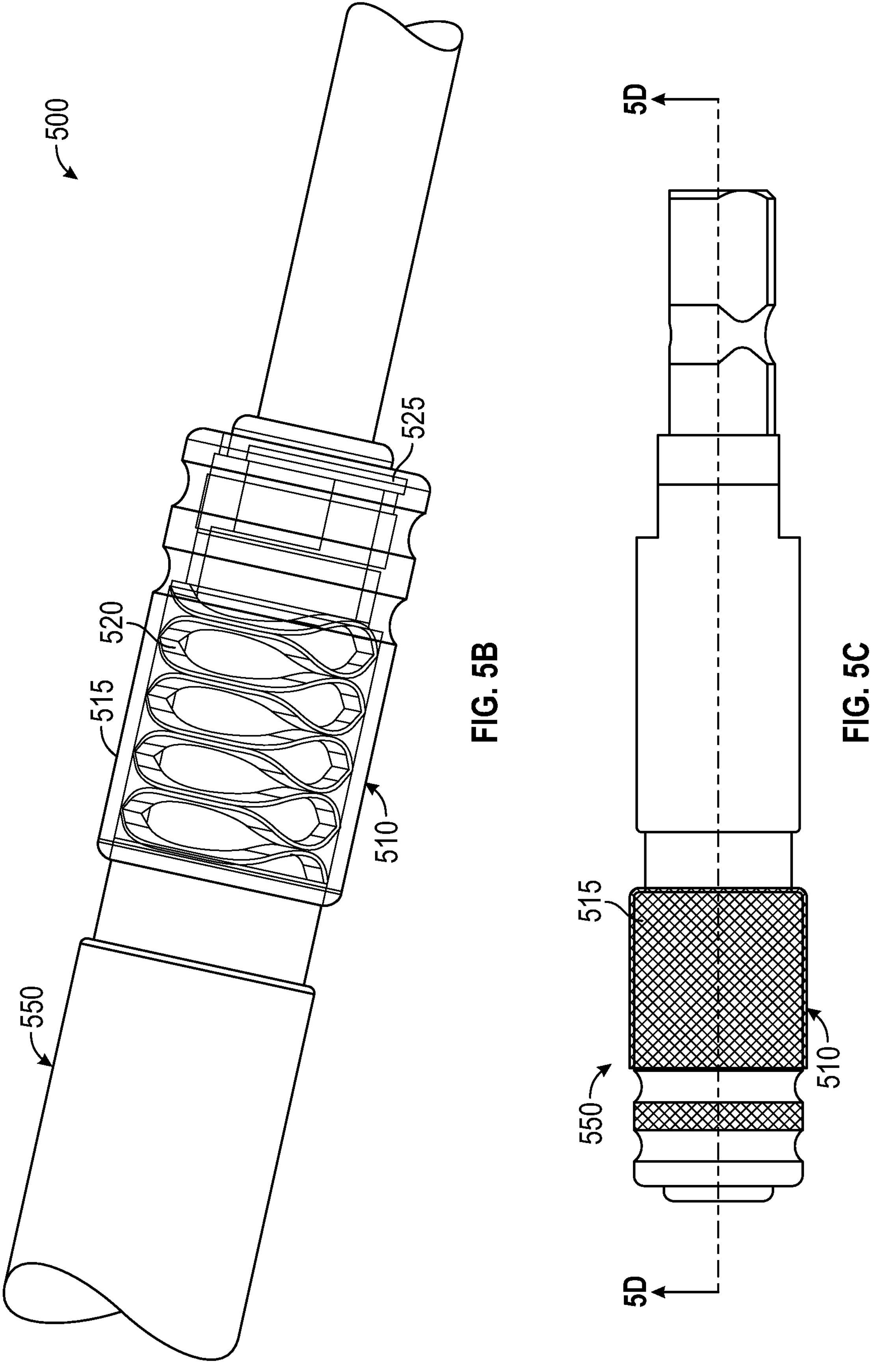
Figure 5D:
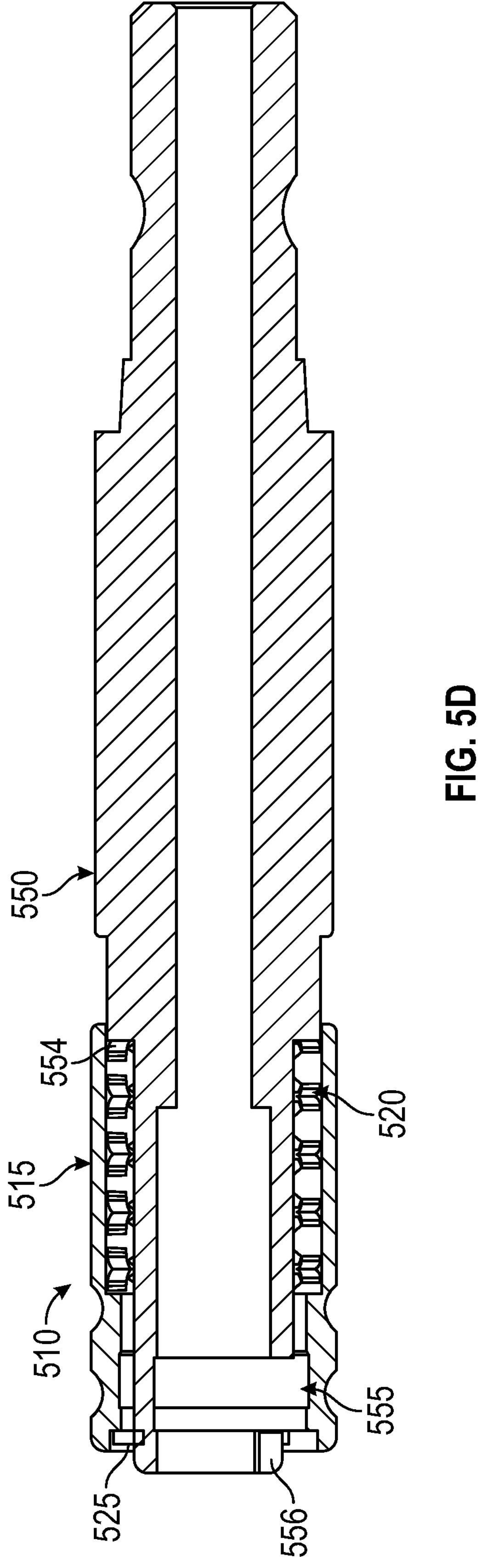

FIG. 5B illustrates some of the inner components of the spring-loaded retention mechanism 510, such as the retention sleeve 515, bias member 520, and lock washer 525. The lock washer 525 holds the retention sleeve 515 in position on the drive adapter 550. The bias member 520, in this example, includes a series of stacked spring washers captured between the retention sleeve 515 and a portion of the drive adapter 550. FIG. 5D is a cross-sectional view that illustrates some additional structures, such as bias member stop 554, the clip channel 555, and the drive retention clip 556. The clip channel 555 is formed from a removed section of the drive adapter that allows the adapter clip 115, 415 to snap onto the reamer shaft 160 (not illustrated here). The drive retention clip 556 was discussed above in reference to FIGS. 3A-3B and drive retention clip 156. As noted above, the drive retention clip 556 is a distal portion of the drive adapter 550 that mirrors adapter clip 115, 415 and holds the measurement instrument 110, 410 in position longitudinally relative to the reaming instrument.

Figure 6:
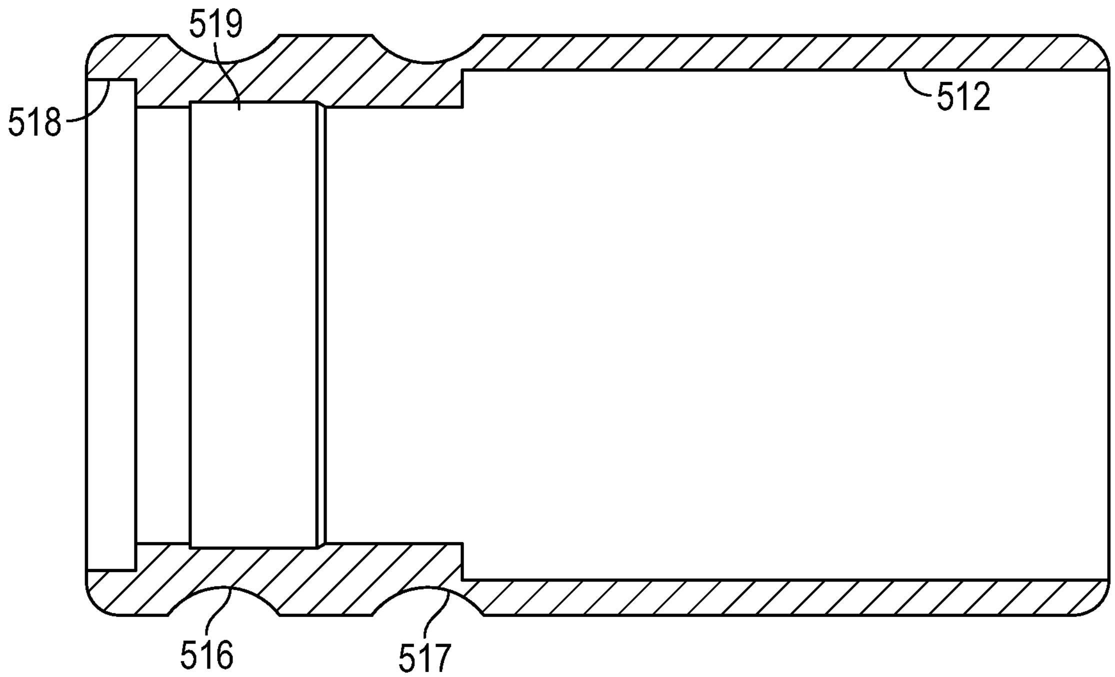
FIG. 6 is a cross-section view of a retention sleeve portion of a spring-loaded adapter for retaining a removable intramedullary measurement instrument, according to an example embodiment.

FIG. 6 is a cross-section view of a retention sleeve 515 portion of a spring-loaded adapter 510 for retaining a removable intramedullary measurement instrument 110, 410, according to an example embodiment. In this example, the retention sleeve 515 includes structures such as grip grooves 516, 517, a washer stop 518, an instrument recess 519 and a bias member recess 521. The grip grooves 516, 517 are radiused circumferential grooves cut into the outer surface of the retention sleeve 515 to assist in manipulating the spring-loaded retention mechanism 510. The washer stop 518 is a circumferential shoulder cut into an inner surface of the retention sleeve 515 to engage with the lock washer 525 to keep the retention sleeve 515 on the drive attachment 550. The instrument recess 519 is a circumferential groove cut into an inner surface of the retention sleeve 515 to provide space for the adapter clip 115, 415. Finally, the bias member recess 521 is an enlarged inner diameter section of the retention sleeve 515 that provides space for the bias member 520.

Figures 7A, 7B:
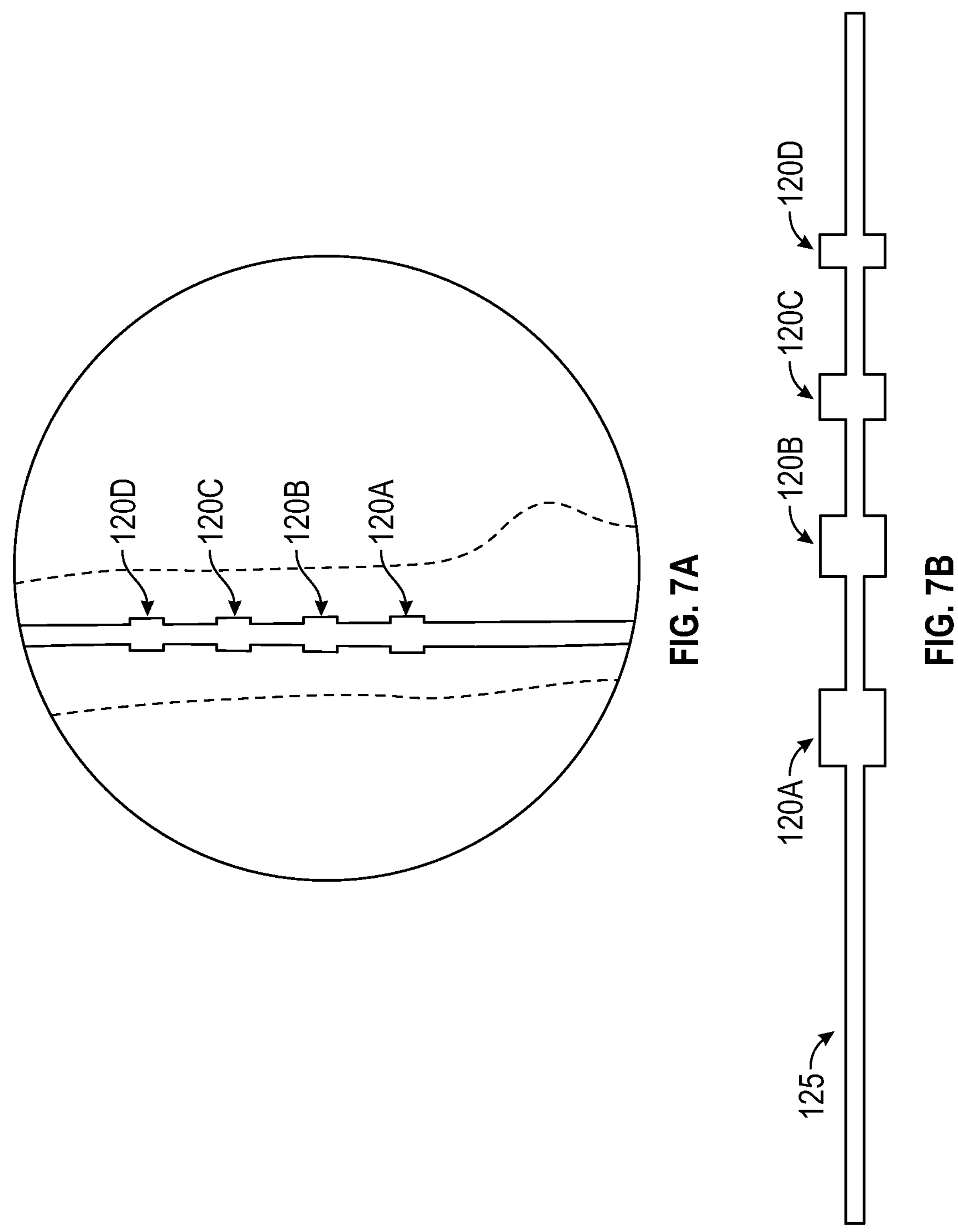
FIGS. 7A-7F are various illustrations of a removable measurement instrument in a medical image, according to various example embodiments.
Figures 7C, 7D, 7E, 7F:
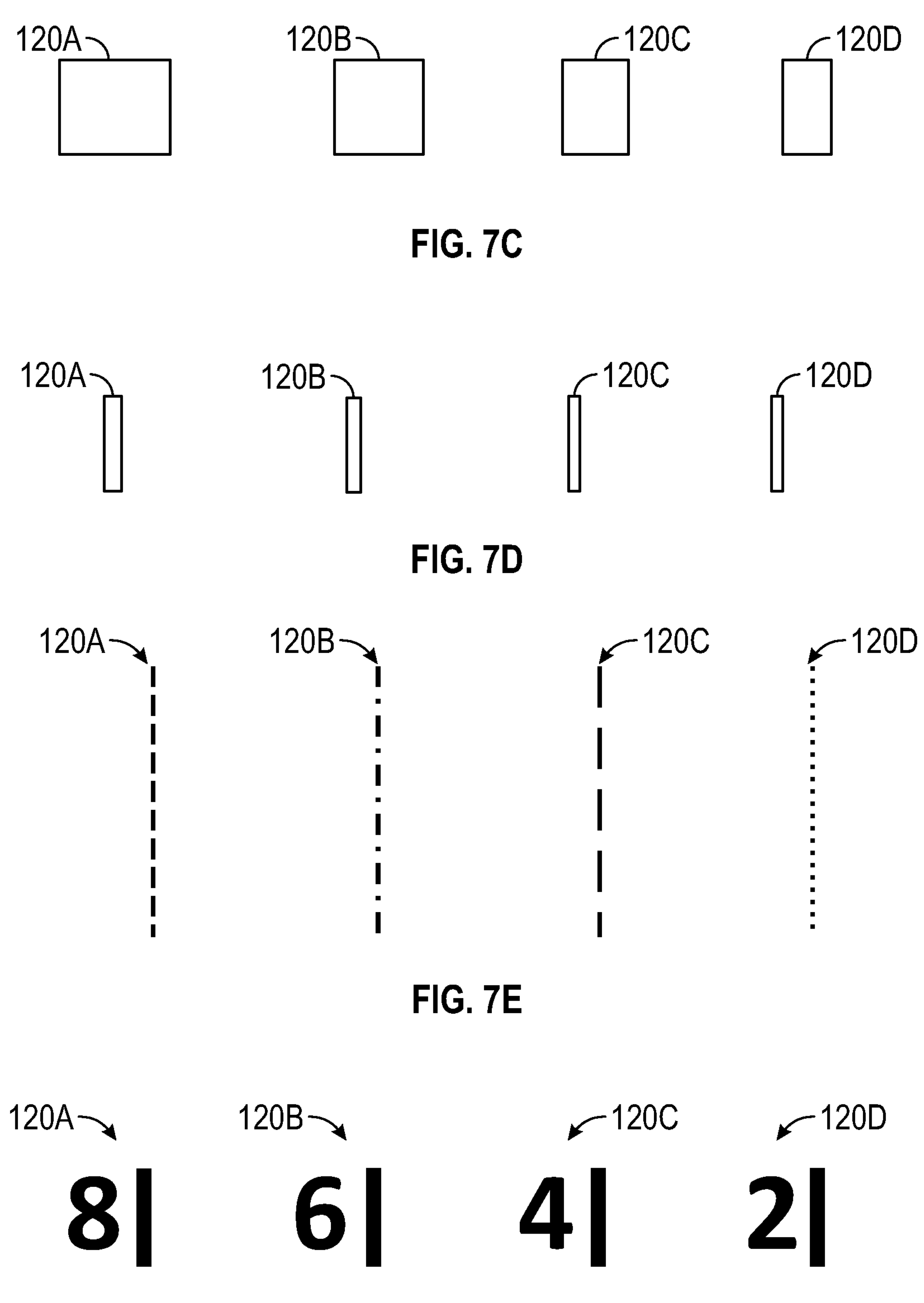

FIGS. 7A-7F are various illustrations depicting a removable measurement instrument 110, 410 in a medical image, according to various example embodiments. The figures are labeled in accordance with measurement instrument 110, but are also representative of how measurement instrument 410 would appear in a medial image, such as a fluoroscopic image. FIG. 7A is an actual fluoroscopic image of a measurement instrument 110, 410 with radiopaque measurement clips 120, 420 and radiopaque elongate body 125, 425. FIGS. 7B-7F are illustrations of alternative concepts for radiopaque materials used within the measurement clips 120, 420. For example, FIG. 7B illustrates different sized measurement clips 120, 420, where the visible width is representative of the relative lengths (large width longer distance). FIG. 7C is a similar arrangement, but with the elongate body 125, 425 not being radiopaque so the measurement clips 120, 420 stand out more in the medical image. FIG. 7D illustrates use of narrower lines to represent each of the measurement clips 120, 420. FIG. 7E introduces the concept of further differentiating measurement clips by different line types. This concept could be extended to include different shape variations, so long as the shapes can provide a defined measurement line. Finally, FIG. 7F introduces the concept of including a number in radiopaque material within the measurement clips.

Figure 8:
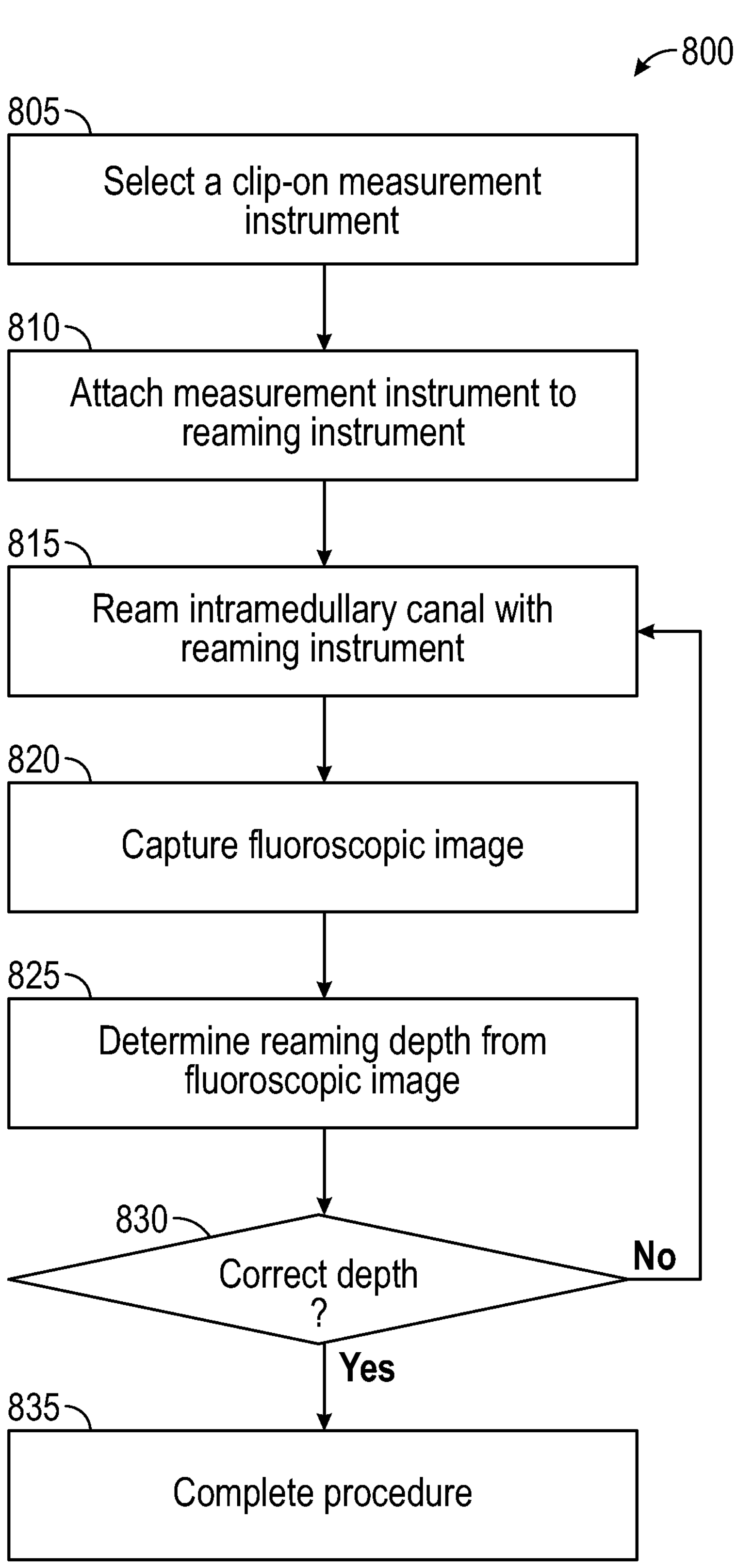
FIG. 8 is a flowchart illustrating an example surgical technique for measuring an intramedullary canal using a removable measurement instrument, according to various example embodiments.

FIG. 8 is a flowchart illustrating an example surgical technique 800 for measuring an intramedullary canal using a removable measurement instrument, such as measurement instrument 110, 410. In this example, the technique 800 can include operations such as selecting a measurement instrument at 805, attaching the measurement instrument at 810, reaming an intramedullary canal at 815, capturing a fluoroscopic image at 820, determining a reaming depth at 825, verifying that the reaming depth is correct at 830, and completing the procedure at 835. The technique 800 can be conducted using any of the clip-on (removable) measurement instruments discussed herein.

In an example, the technique 800 can begin at 805 with the provider selecting an appropriate clip-on measurement instrument, such as measurement instrument 110. At 810, the technique 800 can continue with the provider attaching the measurement instrument 110 to a reaming instrument. In this example, attaching the measurement instrument 110 can include inserting the adapter clip 115 into the clip channel 115 and snapping the measurement clips 120 onto the shaft 160 of the reaming instrument. At 815, the technique 800 can continue with the provider using the reaming instrument with the measurement instrument 110 attached to ream an intramedullary canal. At 820, the technique 800 continues with the provider capturing a medical image (e.g., a fluoroscopic image) of the reaming instrument with the measurement instrument in the intramedullary canal. Once the medical image is captured, the technique 800 can continue at 825 with the provider identifying the measurement clip 120 on the measurement instrument 110 that aligns with the appropriate bone landmark, which allows for determining the length of the reamed intramedullary canal. The length of the reamed intramedullary canal relates to the length of an intramedullary nail. At 830, the technique 800 can continue with the provider judging whether the reaming depth is correct or sufficient for the intended procedure (e.g., will the desired nail fit in the canal). If the reaming depth is not sufficient for the intended nail length, the provider can select a different size and proceed to operation 835, or optionally, the technique 800 can return to operation 815 for additional reaming. If the reaming depth is sufficient, then the technique 800 can proceed to operation 835 with the provider completing the procedure, which can include removing the reaming instrument and implanting an intramedullary nail, among other things.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed. Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An intramedullary reaming instrument, the instrument comprising:

an adapter interface adapted to receive a handle or couple to a power head;

an elongate shaft coupled to a distal end of the adapter interface and extending along a longitudinal axis of the instrument;

a reaming tip coupled to a distal end of the elongate shaft; and a removable intramedullary canal measurement device comprising:

an elongate body extending from a first end to a second end along the longitudinal axis when attached to the instrument;

an adapter clip extending from the first end configured to secure the measurement device to the adapter interface; and a plurality of measurement clips including at least three measurement clips distributed along the elongate body at predetermined distances from the reaming tip when the measurement device is secured to the instrument, each measurement clip of the plurality of measurement clips configured to engage a shaft of the instrument, wherein the adapter interface includes a locking collar disposed around a distal end of the adapter interface and configured to secure the adapter clip of the measurement device; and wherein the locking collar is a cylinder including an inner circumferential lip to receive a bias member configured to bias the locking collar into position over the adapter clip.

2. The intramedullary reaming instrument of claim 1, wherein the adapter interface includes a standard power drill adapter selected from a group of power drill adapters including:

a Hudson adapter;

a large AO adapter;

a small AO adapter, and a Zimmer Hall adapter.

3. The intramedullary reaming instrument of claim 1, wherein each measurement clip of the plurality of measurement clips includes a pair of opposing semi-circular arms forming a C-shape structure extending from the elongate body transverse to the longitudinal axis.

4. The intramedullary reaming instrument of claim 3, wherein the pair of opposing semi-circular arms forming each measurement clip are configured to receive the elongate shaft of the intramedullary reaming instrument.

5. The intramedullary reaming instrument of claim 4, wherein the pair of opposing semi-circular arms are formed from a flexible material configured to generate a friction fit around the elongate shaft of the intramedullary reaming instrument.

6. The intramedullary reaming instrument of claim 5, wherein a distal most measurement clip on the distal end of the measurement device includes the friction fit, while all remaining measurement clips of the plurality of measurement clips are configured to receive the shaft of the reaming instrument without a friction fit.

7. The intramedullary reaming instrument of claim 1, wherein each measurement clip of the plurality of measurement clips includes at least a radiopaque portion configured to present a distinct visual signature within a fluoroscopic medical image.

8. The intramedullary reaming instrument of claim 7, wherein the radiopaque portion includes numbers presentative of a length of measurement associated with each measurement clip.

9. The intramedullary reaming instrument of claim 7, wherein the radiopaque portion includes a different length or thickness for each measurement clip of the plurality of measurement clips.

10. The intramedullary reaming instrument of claim 1, each measurement clip of the plurality of measurement clips is configured to represent a common intramedullary nail length when the measurement device is attached to the reaming instrument.

11. The intramedullary reaming instrument of claim 10, wherein the plurality of measurement clips includes four measurement clips.

12. The intramedullary reaming instrument of claim 11, wherein the plurality of measurement clips are positioned along the elongate body to represent 4 common intramedullary nail lengths including 320 mm, 340 mm, 360 mm, and 380 mm.

13. The instrument of claim 1, wherein the locking collar is retained on the adapter interface by a locking washer engaging a distal end of the adapter interface and a distal end of the locking collar.

* * * * *